United States Patent [19]

Matsuda et al.

[11] 4,163,755

[45] Aug. 7, 1979

[54] PROCESSING OF ACRYLAMIDE SOLUTIONS; CONCENTRATION WITHOUT POLYMER FORMATION

[75] Inventors: Ken Matsuda; Martin S. Butensky, both of Stamford; Kin H. Tsu, Norwalk; Robert J. Munch, Stamford, all of Conn.

[73] Assignee: American Cyanamid Company, Stamford, Conn.

[21] Appl. No.: 759,318

[22] Filed: Jan. 13, 1977

Related U.S. Application Data

[63] Continuation of Ser. No. 604,379, Aug. 13, 1975, which is a continuation of Ser. No. 410,456, Oct. 29, 1973, abandoned.

[51] Int. Cl.² .............. C07C 103/133; C07C 103/00; B01D 1/00; B01D 1/16
[52] U.S. Cl. ............................ 260/561 N; 159/48 L; 159/47 R; 23/302 A; 159/DIG. 10; 203/86; 203/9

[58] Field of Search .................. 203/86, 9; 23/302 A; 260/561 N, DIG. 22; 159/DIG. 10, 47 R, 48 R, 48 L

[56] References Cited

U.S. PATENT DOCUMENTS

| | | | |
|---|---|---|---|
| 2,771,490 | 11/1956 | Stoddard | 23/302 A |
| 2,800,434 | 7/1957 | Howlett | 203/86 |
| 3,324,180 | 6/1967 | Beer | 23/302 A |
| 3,493,471 | 2/1970 | Bashaw | 203/86 |
| 3,546,289 | 12/1970 | Kiikka | 23/302 A |
| 3,549,706 | 12/1970 | Takaki | 23/302 A |
| 3,699,081 | 10/1972 | Iwashito | 23/302 A |
| 3,887,425 | 6/1975 | Munch | 159/47 R |
| 3,917,693 | 11/1975 | Asano | 260/561 N |

OTHER PUBLICATIONS

Perry's Chem. Engrs' Handbook, 4th Ed., McGraw-Hill, 1963, pp. 23-28.

*Primary Examiner*—Stephen J. Emery
*Attorney, Agent, or Firm*—Gordon L. Hart

[57] ABSTRACT

Use of copper ion in acrylamide solution during concentration to inhibit polymerization.

5 Claims, No Drawings

PROCESSING OF ACRYLAMIDE SOLUTIONS; CONCENTRATION WITHOUT POLYMER FORMATION

This a continuation of application Ser. No. 604,379, filed Aug. 13, 1975 which was a continuation copending with application Ser. No. 410,456 filed Oct. 29, 1973, now abandoned.

The invention relates to concentrating aqueous acrylamide solutions by evaporation of water from said solution. An object of the invention is to provide a process for concentrating acrylamide solutions without causing unwanted polymerization of acrylamide in the solution during the concentration process.

An evaporation process for concentrating and drying aqueous acrylamide was described in Belgium Pat. No. 792,339, in which air was introduced into the evaporator at a rate of at least 0.1 mole air per mole of water evaporated. In a United States patent application by the co-inventor Robert J. Munch, titled "Concentrating Acrylamide Solutions" filed in the U.S. Patent Office Oct. 1, 1973 another process was described for concentrating acrylamide aqueous solutions by vacuum flash evaporation to remove part of the water while avoiding accumulations of residue solution in the evaporator and rapidly restoring oxygen to saturation in the liquid concentrate as it is returned to atmospheric pressure.

Cupric ion is a known polymerization inhibitor for use in aqueous acrylamide solutions but it seemed impractical at first to incorporate soluble salts of copper in the solution because they were found to precipitate as basic salts and cause serious corrosion of stainless steel surfaces in heated lines and vessels containing the acrylamide solutions. We discovered however that when aqueous acrylamide solutions containing cupric ion are maintained at pH value of pH5 or less the precipitation of the copper salt and therefore the corrosion of stainless steel surfaces is effectively inhibited.

In accordance with the invention, the concentrating of aqueous acrylamide solution by flash evaporation of water from such solutions is carried out with the pH of such solutions at a value of pH 5 or less and with cupric ion present in said solution in the range from 5 to 200 parts copper per million parts acrylamide (5-200 ppm $Cu^{+2}$/AMD) in the solution. In preferred embodiments, the solutions are also saturated with air while they are not in the flash evaporator.

Reference is made to the aforementioned United States patent application titled "Concentrating Acrylamide Solutions" for description of apparatus and process that would be suitable for use in carrying out the present process. In a process of the kind described, copper sulfate and sulfuric acid are added to the acrylamide solution in the evaporator, or to the recycle stream, as needed to maintain the selected pH value and the selected cupric ion concentration in the evaporator or the circulating recycle stream. In addition to the inhibiting effect of oxygen in the solution, which is described in more detail in the Munch application, the present invention provides the inhibiting effect of copper, which has the advantage over oxygen in the present process of not evaporating during the flash evaporation of water from the solution.

In a preferred embodiment of the invention, both oxygen and cupric ion are used in combination as inhibitors in acrylamide solutions during the process of concentrating the solutions. The combination of inhibitors has the advantages that the copper inhibitor is present in the solution both during and after the flash evaporation which removes oxygen. On the other hand, by restoring and maintaining absorbed oxygen in the solution outside the evaporator, only a minimum quantity of copper has to be used. This is particularly important if the product solution is to be used for making polyacrylamide, in which case the cupric ion must be removed before polymerization. Keeping the cupric ion concentration low lessens the work of removing it, as by ion exchange or other appropriate means when the solution is to be used for polymerization.

With cupric ion present in the solution, the criticality of short residence time in the evaporator is less severe and the extreme means for evacuating the liquid residue as quickly as possible and washing the evaporator walls to prevent accumulation, as described in the Munch application, become less important. For example, instead of the barometric leg for exit of the liquid residue as described in the earlier application, it is found quite practical to substitute conventional pressure pumps to bring the residue from the flash evaporator to atmospheric pressure. Furthermore, the necessity for avoiding accumulation of liquid residue in the vessel is less critical and when the residue has been restored to atmospheric or higher pressure, oxygen can be restored in the solution by contact with air which can be directly injected into a line carrying the liquid residue. Thus, the invention provides a significant improvement of the process described in the Munch application.

In the following example, cupric ion is added as cupric sulfate and sulfuric acid is used to adjust pH. While these are the preferred salt and acid for the process, the invention needs not be limited to the embodiment using the sulfate salt and acid; another soluble cupric salt or another acid may be used if desired. Other suitable cupric salts include copper nitrate, copper acetate, and the like and other suitable acids include nitric and acetic acids and the like. For the following example a 30% acrylamide aqueous solution is condensed to make a 50% solution but the same process is useful for condensing solutions in the range from 5–50% acrylamide to make more concentrated solutions.

EXAMPLE

A 30% acrylamide aqueous solution is concentrated to make 50% acrylamide aqueous solution in laboratory apparatus having elements corresponding to those described in the aforementioned Munch application. The recirculating solution to the evaporator is continuously adjusted to pH5 with sulfuric acid. Cupric sulfate is added to maintain concentration of 50 ppm $Cu^{+2}$/AMD in the evaporator. The feed is led into a vacuum flash evaporator in which the pressure has been reduced to maintain a boiling point of acrylamide aqueous solution at about 80° C. inside the vessel (about 300 mm Hg). Liquid residue from the evaporation is removed to atmospheric pressure and contacted with air to restore oxygen to saturation in the solution. Rate of recycle of liquid residue to the evaporator, which is preheated to 85° C. before reentry is adjusted to make a constant 50% acrylamide residue at the selected fresh feed rate, which is balanced with the designed water vaporization rate and the product withdrawal rate. In runs where sulfuric acid was not added (solution pH about 6–7) it was found that stainless steel surfaces contacting the process solution were corroded by pitting, particularly at heat exchange surfaces where cupric solids were precipitated. Adjustment to pH5 in the liquid residue was found to eliminate this corrosion problem.

In the runs of the kind described with several variations it was found that the inhibiting effect of cupric ion is effective at any of several concentrations in the range from about 5 to 200 ppm Cu. Because the copper ion remains in the acrylamide solution during its pass through the evaporator, it is not so critical to remove the solution from the evaporator and restore oxygen as quickly as was necessary when only oxygen inhibitor is used. It is found that the residue can be allowed to accumulate in the bottom of the evaporator and can be removed therefrom by a pump rather than through the barometric arm described in the earlier application. It is preferred to use no more than the minimum effective amount of cupric ion as it has to be removed from the solution to meet certain product specifications. This is done by ion exchange resin, for example, and the least amount of copper is most easily removed. It is preferred to use no more acid than necessary to avoid excessively low pH in the product acrylamide. Operation at about pH5 is found satisfactory although a lower pH value could be used.

Because of the presence of cupric ion it is easier to avoid polymerization in the evaporator at higher operating temperatures so it becomes more practical to operate the flash evaporator with higher boiling temperature at less vacuum, if desired. It is quite possible even to operate the flash evaporator at atmospheric pressure with superheated feed, although this is not usually the most preferred mode of operation. The invention can be used at any evaporation pressure from about 70 mm Hg absolute up to atmospheric pressure, or even higher if desired. Under the operating conditions contemplated the mole ratio of air to water vapor in the vapor phase inside the flash evaporation chamber is much below 0.1, usually in the magnitude about 0.005 and generally in the range from about 0.05 to about 0.001. The boil up rate is generally in the range from about one-third to about four parts by wt. water per 100 parts of liquid circulated. The boil up rate is controlled by the recycle feed entry temperature, usually in the range from 5-20 degrees higher than the boiling point in the evaporator. Calculated residence time is preferably about 20 minutes but may range up to as much as 250 minutes. Cupric ion should be kept to the minimum practical concentration usually in the range from about 5-200 ppm.

In some processes embodying the invention, oxygen is restored to the solution by injecting air directly into the recycle lines carrying liquid residue from the evaporator. To avoid carrying undissolved air from the lines into the evaporator with the liquid feed, it is preferred to pass the recycle stream through a phase separation vessel to permit excess air to separate before the liquid is led to the evaporator. This avoids unnecessary load on the vacuum pumps. The separator is simply a container with air space above the liquid level to receive any air that bubbles from the liquid.

We claim:

1. In a process of concentrating acrylamide aqueous solution from less than 50% acrylamide to more concentrated liquid aqueous solution by flash evaporation of water from the solution at reduced pressure below atmospheric in evaporation apparatus having stainless steel surfaces contacting the concentrated solution, the improvement wherein cupric ion is in the concentrated liquid solution in the range from 5 to 200 parts copper per million parts acrylamide present as cupric salt dissolved in said concentrated solution and the pH value in said concentrated solution is maintained at pH5 or less.

2. An improved process defined by claim 1 wherein the defined soluble cupric salt is cupric sulfate and the defined pH value is maintained by addition of sulfuric acid.

3. An improved process defined by claim 1 wherein at least a part of the residue liquid from the evaporator is saturated with air at atmospheric pressure and then heated and recycled to the evaporator.

4. An improved process defined by claim 1 wherein the defined reduced pressure is about 300 mm Hg absolute.

5. An improved process defined by claim 2 wherein the selected pH is about 5 and the flash evaporation is carried out at about 300 mm Hg absolute, and air is contacted with the liquid residue taken from the evaporator to restore saturation of oxygen in the solution at atmospheric pressure.

* * * * *